US009113943B2

(12) United States Patent
Ross et al.

(10) Patent No.: US 9,113,943 B2
(45) Date of Patent: Aug. 25, 2015

(54) ULTRASONIC SURGICAL INSTRUMENTS

(75) Inventors: Anthony B. Ross, Boulder, CO (US);
Robert B. Stoddard, Steamboat Springs, CO (US); James S. Cunningham, Boulder, CO (US);
William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Arlen K. Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 258 days.

(21) Appl. No.: 13/435,835

(22) Filed: Mar. 30, 2012

(65) Prior Publication Data
US 2012/0253371 A1    Oct. 4, 2012

Related U.S. Application Data

(60) Provisional application No. 61/469,572, filed on Mar. 30, 2011.

(51) Int. Cl.
*A61B 17/32* (2006.01)
*A61B 17/16* (2006.01)

(52) U.S. Cl.
CPC . *A61B 17/320092* (2013.01); *A61B 2017/1651* (2013.01); *A61B 2217/007* (2013.01)

(58) Field of Classification Search
CPC ............... A61B 17/320092; A61B 2017/1651; A61B 2217/007

USPC ............. 606/169, 170, 171, 128, 51, 52
See application file for complete search history.

(56) References Cited

U.S. PATENT DOCUMENTS

| | | |
|---|---|---|
| 5,346,502 A | 9/1994 | Estabrook et al. |
| 5,776,155 A | 7/1998 | Beaupre et al. |
| 5,810,859 A | 9/1998 | DiMatteo et al. |
| 5,873,873 A | 2/1999 | Smith et al. |
| 5,897,569 A | 4/1999 | Kellogg et al. |
| 5,944,737 A | 8/1999 | Tsonton et al. |
| 5,968,060 A | 10/1999 | Kellogg |

(Continued)

FOREIGN PATENT DOCUMENTS

| | | |
|---|---|---|
| AU | 731135 | 3/2001 |
| CA | 2 247 149 | 6/2007 |

(Continued)

OTHER PUBLICATIONS

U.S. Appl. No. 13/108,117, filed May 16, 2011, Andrey Balanev.
(Continued)

*Primary Examiner* — Katrina Stransky

(57) ABSTRACT

An ultrasonic surgical instrument is provided. The ultrasonic surgical instrument includes a housing having an elongated shaft extending therefrom. The shaft defines a longitudinal axis therethrough and has a jaw member disposed at a distal end thereof. The jaw member is movable between an open configuration and a clamping configuration. A cutting blade extends from a distal end the shaft and operably couples to the housing and adjacent the jaw member. The cutting blade includes top and bottom portions. The top portion configured to cool the bottom portion while the cutting blade treats tissue.

18 Claims, 3 Drawing Sheets

(56) References Cited

U.S. PATENT DOCUMENTS

| | | |
|---|---|---|
| 5,980,510 A | 11/1999 | Tsonton et al. |
| 5,989,275 A | 11/1999 | Estabrook et al. |
| 6,051,010 A | 4/2000 | DiMatteo et al. |
| 6,061,551 A | 5/2000 | Sorrells et al. |
| 6,063,098 A | 5/2000 | Houser et al. |
| 6,068,647 A | 5/2000 | Witt et al. |
| 6,239,044 B1 | 5/2001 | Kashiwagi et al. |
| 6,251,110 B1 | 6/2001 | Wampler |
| 6,257,241 B1 | 7/2001 | Wampler |
| 6,274,963 B1 | 8/2001 | Estabrook et al. |
| 6,287,344 B1 | 9/2001 | Wampler et al. |
| 6,425,906 B1 | 7/2002 | Young et al. |
| 6,425,912 B1 | 7/2002 | Knowlton |
| 6,491,708 B2 | 12/2002 | Madan et al. |
| 6,514,249 B1 | 2/2003 | Maguire et al. |
| 6,541,780 B1 | 4/2003 | Richards et al. |
| 6,547,788 B1 | 4/2003 | Maguire et al. |
| 6,869,431 B2 | 3/2005 | Maguire et al. |
| 7,135,029 B2 | 11/2006 | Makin et al. |
| 7,270,656 B2 | 9/2007 | Gowda et al. |
| 7,275,440 B2 | 10/2007 | Gunnerman et al. |
| 7,530,986 B2 | 5/2009 | Beaupre et al. |
| 7,533,830 B1 | 5/2009 | Rose |
| 7,559,241 B2 | 7/2009 | Gunnerman |
| 2003/0114874 A1 | 6/2003 | Craig et al. |
| 2005/0049546 A1 | 3/2005 | Messerly et al. |
| 2007/0173746 A1 | 7/2007 | Barzilay et al. |
| 2007/0225618 A1 | 9/2007 | Ward et al. |
| 2008/0234709 A1 | 9/2008 | Houser |
| 2008/0234710 A1 | 9/2008 | Neurohr et al. |
| 2009/0030437 A1 | 1/2009 | Houser et al. |
| 2009/0036913 A1 | 2/2009 | Wiener et al. |
| 2009/0036914 A1 * | 2/2009 | Houser ............ 606/169 |
| 2009/0143795 A1 * | 6/2009 | Robertson ............ 606/169 |
| 2009/0143806 A1 * | 6/2009 | Witt et al. ............ 606/169 |
| 2009/0149797 A1 | 6/2009 | Dacey, Jr. et al. |
| 2009/0149798 A1 | 6/2009 | Dacey, Jr. et al. |
| 2009/0177218 A1 | 7/2009 | Young et al. |
| 2009/0177219 A1 | 7/2009 | Conlon |
| 2009/0209900 A1 | 8/2009 | Carmeli et al. |
| 2009/0216157 A1 * | 8/2009 | Yamada ............ 601/2 |
| 2011/0241786 A1 | 10/2011 | Gilbert |

FOREIGN PATENT DOCUMENTS

| | | |
|---|---|---|
| CA | 2 261 505 | 8/2009 |
| EP | 0 908 148 | 1/2002 |
| EP | 0 908 152 | 1/2002 |
| EP | 0 908 153 | 12/2002 |
| EP | 0 908 154 | 5/2003 |
| EP | 0 908 155 | 6/2003 |
| EP | 0 908 149 | 7/2003 |
| EP | 1 334 697 | 8/2003 |
| EP | 0 908 151 | 1/2004 |
| EP | 0 893 971 | 4/2004 |
| EP | 1 362 555 | 6/2005 |
| EP | 1 025 806 | 4/2006 |
| EP | 1 040 792 | 5/2010 |
| EP | 1 656 895 | 6/2010 |
| EP | 1 844 720 | 5/2011 |
| GB | 2 333 709 | 8/1999 |
| JP | 2000237204 | 9/2000 |
| WO | WO 98/27874 | 7/1998 |
| WO | WO 98/27875 | 7/1998 |
| WO | WO 98/37815 | 9/1998 |
| WO | WO 98/37819 | 9/1998 |
| WO | WO 99/35982 | 7/1999 |
| WO | WO 99/52489 | 10/1999 |
| WO | WO 03/039429 | 5/2003 |

OTHER PUBLICATIONS

U.S. Appl. No. 13/149,570, filed May 31, 2011, William N. Gregg.
U.S. Appl. No. 13/189,670, filed Jul. 25, 2011, Sean T. Dychus.
U.S. Appl. No. 13/248,402, filed Sep. 29, 2011, Stoddard et al.
U.S. Appl. No. 13/294,743, filed Nov. 11, 2011, Misuchenko et al.
U.S. Appl. No. 13/360,910, filed Jan. 30, 2012, Balanev et al.

* cited by examiner

ULTRASONIC SURGICAL INSTRUMENTS

CROSS-REFERENCE TO RELATED APPLICATION

The present application claims the benefit of and priority to U.S. Provisional Application No. 61/469,572 filed on Mar. 30, 2011 by Ross et al., the entire contents of which is incorporated herein by reference.

BACKGROUND

1. Technical Field

The present disclosure relates to ultrasonic surgical instruments. More particularly, the present disclosure relates to ultrasonic surgical instruments configured to minimize heat damage to tissue adjacent the tissue of interest prior to, during, or following an ultrasonic treatment.

2. Description of Related Art

Ultrasonic energy-powered instruments configured to cut and/or fragment tissue are known in the art. Ultrasonic instruments, typically, include a transducer that is coupled to a probe/waveguide having an active member (e.g., cutting blade, shear, hook, ball, etc.) at a distal end thereof. In use, ultrasonic energy is utilized to vibrate (e.g., at frequency usually in the range of 20 KHz to 60 KHz) the active member to treat tissue of interest.

Ultrasonic instruments may include any of a variety of probe configurations to achieve a specific surgical result. For example, the probe configuration may include an active member in the form of a cutting blade that is combined with a movable jaw configured to grasp and/or manipulate tissue. Such ultrasonic instruments are primarily used in a variety of medical procedures including open surgical procedures, luminal procedures, and endoscopic procedures.

During use, the active member, e.g., the cutting blade, may reach temperatures greater than 200° C. At such temperatures, inadvertent contact between the cutting blade and tissue may cause undesirable heat damage. Moreover, because of the relatively high thermal mass of the cutting blade (e.g., the cutting blade is formed from solid material), the cooling time of the cutting blade is relatively high, which, in turn, may increase the risk of undesirable heat damage to surrounding tissue.

SUMMARY

In view of the foregoing, ultrasonic instruments configured to minimize heat damage to tissue adjacent tissue of interest that has been ultrasonically treated may prove useful in the medical art.

Embodiments of the present disclosure are described in detail with reference to the drawing figures wherein like reference numerals identify similar or identical elements. As used herein, the term "distal" refers to a portion that is being described which is further from a user, while the term "proximal" refers to a portion that is being described which is closer to a user.

An aspect of the present disclosure provides an ultrasonic surgical instrument. The ultrasonic surgical instrument includes a housing having an elongated shaft extending therefrom. The shaft defines a longitudinal axis therethrough and has a jaw member disposed at a distal end thereof. The jaw member is movable between an open configuration and a clamping configuration. A lever may be operably coupled to the housing and is configured to move the jaw member between the open configuration and clamping configuration. A cutting blade extends from a distal end the shaft and operably couples to the housing and adjacent the jaw member. The cutting blade includes top and bottom portions. The top portion configured to cool the bottom portion while the cutting blade treats tissue.

The top portion may be formed from a material that is different from a material that forms the bottom portion. The material that forms the top portion may be a porous ceramic material and/or a porous metal material. The material that forms the bottom portion is selected from the group consisting of stainless steel and titanium.

The top portion may include at least one channel that extends along the longitudinal axis and the length of the top portion. Alternatively, the top portion may include at least one groove that extends perpendicular to the longitudinal axis and towards the bottom portion. The groove(s) may be further defined by a plurality of grooves that are positioned along nodes of the top portion of cutting blade.

The ultrasonic surgical instrument may further include a fluid reservoir housing at least one fluid therein. The fluid reservoir may be in fluid communication with at least one fluid conduit that extends through the shaft. The fluid conduit(s) may have a distal end positioned adjacent the top portion of the cutting blade for providing the at least one fluid to thereto.

The jaw member may include at least one temperature sensor thereon configured to detect a temperature of the bottom portion of the cutting blade. The temperature sensor(s) may be a thermocouple and/or a thermistor. The sensor(s) may communicate a detected temperature of the bottom portion to a controller operably associated with a generator of the ultrasonic surgical instrument. The controller(s) may be configured to determine the temperature of the bottom portion of the cutting blade. When the bottom portion of the cutting blade exceeds a predetermined temperature, the controller may be configured to send a command signal to the fluid reservoir calling for the fluid(s) to be delivered to the top portion of the cutting blade.

An aspect of the present disclosure provides an ultrasonic surgical instrument. The ultrasonic surgical instrument includes a housing having an elongated shaft extending therefrom. The shaft defines a longitudinal axis therethrough and has a jaw member disposed at a distal end thereof. The first jaw member is movable between open and clamping configurations. A cutting blade extends from a distal end the shaft and operably couples to the housing and adjacent the jaw member. The cutting blade includes a top portion formed of a porous material and a bottom portion formed of a solid material. The top portion is configured to cool the bottom portion while the cutting blade treats tissue.

The material that forms the top portion may be a porous ceramic material and/or a porous metal material. The material that forms the bottom portion is selected from the group consisting of stainless steel and titanium.

An aspect of the present disclosure provides an ultrasonic surgical instrument. The ultrasonic surgical instrument includes a housing having an elongated shaft extending therefrom. The shaft defines a longitudinal axis therethrough and has a jaw member disposed at a distal end thereof. The jaw member is movable between an open configuration and a clamping configuration. A lever may be operably coupled to the housing and is configured to move the jaw member between the open configuration and clamping configuration. A cutting blade extends from a distal end the shaft and operably couples to the housing and adjacent the jaw member. The cutting blade includes top and bottom portions. The top portion configured to cool the bottom portion while the cutting blade treats tissue. A fluid reservoir houses at least one fluid therein and is configured to provide at least one fluid to the top portion of the cutting blade to cool the bottom portion prior to, during, and/or after the cutting blade treats tissue.

The fluid reservoir may be in fluid communication with at least one fluid conduit that extends through the shaft. The fluid conduit(s) may have a distal end positioned adjacent the top portion of the cutting blade for providing the at least one fluid thereto. The jaw member may include at least one temperature sensor thereon configured to detect a temperature of the bottom portion of the cutting blade. The temperature sensor(s) may be a thermocouple and/or a thermistor.

The sensor(s) may communicate a detected temperature of the bottom portion to a controller operably associated with a generator of the ultrasonic surgical instrument. The controller(s) may be configured to determine the temperature of the bottom portion of the cutting blade. When the bottom portion of the cutting blade exceeds a predetermined temperature, the controller may be configured to send a command signal to the fluid reservoir calling for the fluid(s) to be delivered to the top portion of the cutting blade.

The top portion may include at least one channel that extends along the longitudinal axis and the length of the top portion. Alternatively, the top portion may include at least one groove that extends perpendicular to the longitudinal axis and towards the bottom portion.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
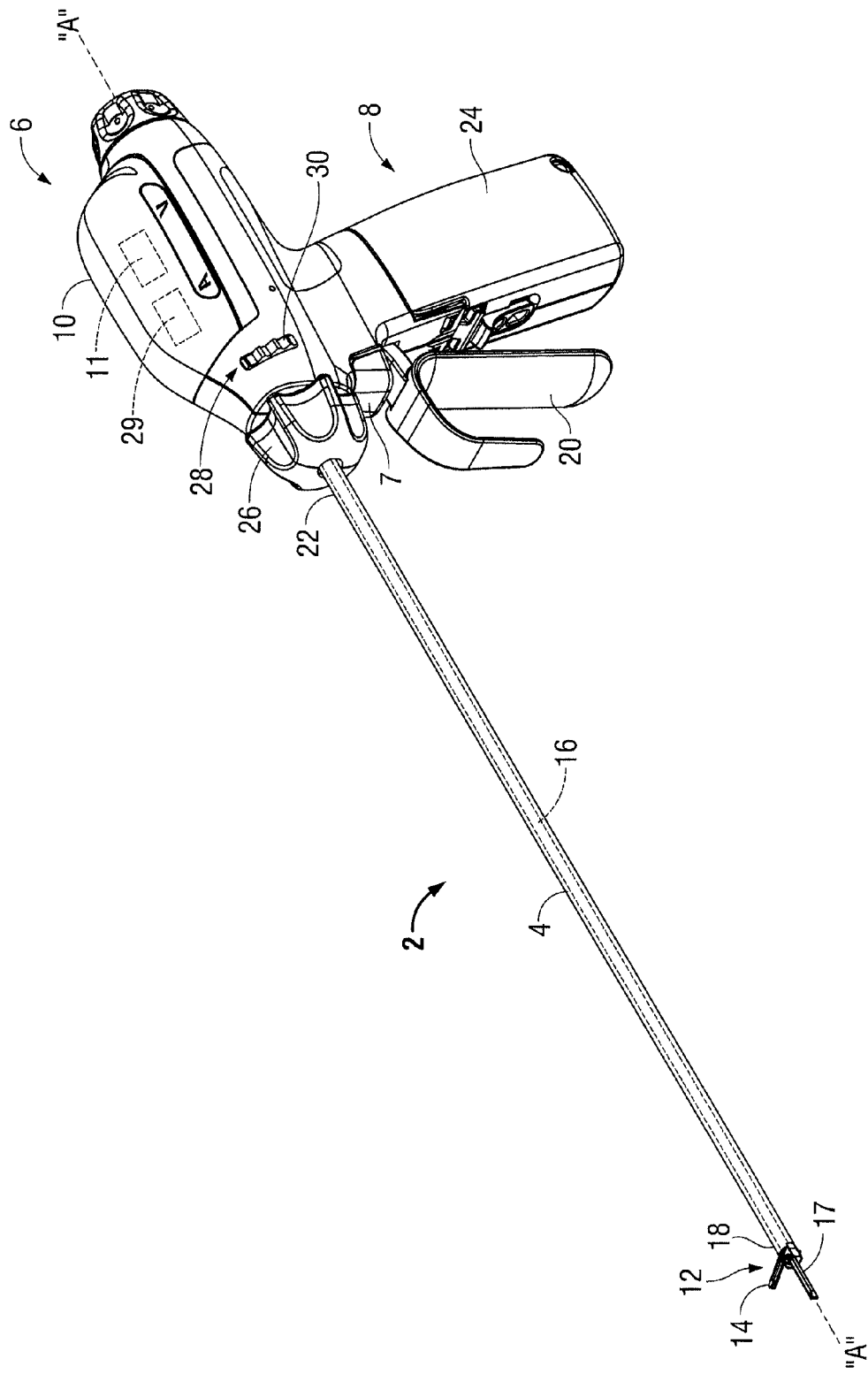
FIG. 1 is a right, perspective view of an ultrasonic instrument according to an embodiment of the present disclosure.

Turning now to FIG. 1, an ultrasonic surgical instrument 2 (instrument 2) according to an embodiment of the present disclosure is illustrated. In the illustrated embodiments, instrument 2 is described herein as being battery powered. Additionally or alternatively, instrument 2 may be externally powered, e.g., via a remote ultrasonic generator that couples to instrument 2.

Briefly, instrument 2 includes a housing 6 configured to house one or more components, e.g., transducer (not explicitly shown), a probe 16, and electrical circuitry that is configured for electrical communication with a battery assembly 8 of instrument 2. A proximal end of housing 6 is configured to releasably couple to an ultrasonic generator 10 and battery assembly 8. A distal end of housing 6 is configured to support and/or couple to a proximal end 22 of a shaft 4 having a longitudinal axis "A-A" defined therethrough. A rotation knob 26 operably couples to housing 6 and is configured to rotate shaft 4 approximately 360° in either direction about the longitudinal axis "A-A." Generator 10 includes the transducer that is coupled to probe 16 via a torque adapter (not explicitly shown) and configured to produce vibratory motion of a cutting blade 17 (FIGS. 1-2) disposed at a distal end of probe 16 when a trigger 7 is depressed. This vibratory motion of cutting blade 17 is utilized to treat tissue of interest. Battery assembly 8 includes a handpiece 24 having a battery (not explicitly shown) operably disposed therein.

Figure 2:
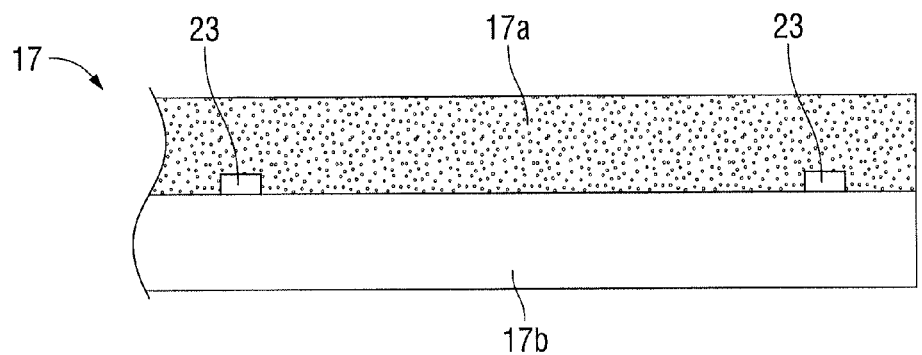
FIG. 2 is an enlarged, side, schematic view of a cutting blade depicted in FIG. 1.

With reference to FIGS. 1-2, an end effector 12 includes a jaw member 14 (FIG. 1) that is supported at a distal end 18 of shaft 4 adjacent cutting blade 17. Jaw member 14 may be pivotably supported at the distal end of the shaft 4 via a pivot pin (not shown) and functions as a "clamping jaw." In particular, jaw member 14 is movable relative to cutting blade 17 (and/or the distal end 18 of the shaft 4) between an open configuration (FIG. 1) and a clamping configuration (not explicitly shown) to clamp tissue when a lever or movable handle 20 (FIG. 1) is actuated. Jaw member 14 and cutting blade 17 are configured to collectively grasp and ultrasonically treat tissue. In particular, with tissue positioned between jaw member 14 and cutting blade 17, the cutting blade is configured to vibrate at a specific frequency (e.g., at a frequency in the range from about 20 KHz to about 60 KHz) to treat tissue.

In accordance with the present disclosure, cutting blade 17 is configured to dissipate heat faster than conventional ultrasonic cutting blades. Specifically, for a given material that forms cutting blade 17, the ability of cutting blade 17 to dissipate heat is directly proportional to the overall thermal mass of cutting blade 17. In accordance with the instant disclosure, the overall thermal mass of cutting blade 17 is reduced by providing a top portion 17a of cutting blade 17 that includes a thermal mass that is less than a thermal mass of a bottom portion 17b of cutting blade 17 (FIG. 2). As a result thereof, the ability of cutting blade 17 to dissipate heat is increased when compared to conventional cutting blades.

Continuing with reference to FIG. 2, an embodiment cutting blade 17 is illustrated. In the embodiment illustrated in FIGS. 1 and 2, cutting blade 17 includes top portion 17a and bottom portion 17b. Bottom portion 17b is configured to treat tissue of interest. To this end, bottom portion 17b may be formed from any suitable material, including but not limited to, metal, ceramic, or other suitable material. In embodiments, bottom portion 17b may be formed from stainless steel or titanium. Metals of this type are suitable for forming bottom portion 17b because of their ability to withstand high temperatures and vibrations that are, typically, associated with cutting blade 17 during operation thereof.

Top portion 17a is configured to facilitate cooling the bottom portion 17b while cutting blade 17 treats tissue. To this end, top portion 17a may be formed from any suitable material including, but not limited to metal, plastic, ceramic, etc. In the embodiment illustrated in FIGS. 1-2, top portion 17a is made from a porous metal or porous ceramic material. The porosity of the metal or ceramic material may be altered to achieve a specific overall thermal mass of cutting blade 17. In one particular embodiment, for example, bottom portion 17*b* may be formed from solid titanium material and top portion 17*a* may be formed from porous titanium material, wherein the specific porosity of the titanium that forms top portion 17*a* may be determined during the manufacturing process of cutting blade 17. As a result thereof, the overall thermal mass of cutting blade 17 is reduced to facilitate cooling thereof.

In some embodiments, it may prove advantageous to fill the pores of top portion 17*a* with one or more suitable fluids. For example, the pores of top portion 17*a* may be filled with saline during the manufacturing process of top portion 17*a*. In this particular embodiment, as bottom portion 17*b* heats-up, the saline is caused to evaporate, which, in turn, facilitates cooling bottom portion 17*b*.

Top and bottom portions 17*a* and 17*b* may be formed as a single component or may be formed as separate components and coupled via one or more suitable coupling methods, e.g., welding, brazing, etc.

In other embodiments, the overall thermal mass of cutting blade 17 may be decreased by providing one or more grooves or channels within top portion 17*a*. For example, in the embodiment illustrated in FIGS. 3 and 4, a top portion 117*a* is provided with a plurality of longitudinal channels 119 that extend along side surfaces of top portion 117*a*, as best seen in FIG. 4. Removing material from top portion 117*a* to form longitudinal channels 119 reduces the overall thermal mass of cutting blade 117. Alternatively, a plurality of grooves 219 that extends perpendicular to the longitudinal axis "A-A" and towards bottom portion 217*b* may be provided on top portion 217*a* (FIG. 5) to reduce the overall thermal mass of cutting blade 217.

Figure 6:
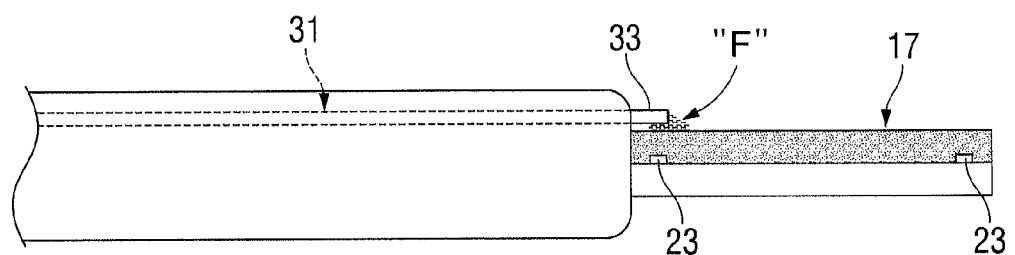
FIG. 6 is an enlarged, side, schematic view of a distal end of an ultrasonic instrument according to an embodiment of the present disclosure.

An optional fluid reservoir 29 (shown in phantom in FIG. 1) may be provided in housing 6 and configured to provide one or more suitable fluids "F" (e.g., saline) to top portions 17*a*, 117*a*, 217*a* (see, e.g., FIGS. 4 and 6). With this purpose in mind, fluid reservoir 29 may operably couple to a fluid conduit (or lumen) 31 (FIG. 6) that extends from housing 6 to distal end 18 of shaft 4 (FIG. 6). In this particular embodiment, a distal end 33 of fluid conduit 31 may be operably supported at distal end 18 adjacent top portion 17*a* and configured to provide fluid(s) "F" to distal ends 17*a*, 117*a*, 217*a* to facilitate cooling bottom portions 17*b*, 117*b*, 217*b*, respectively.

In the embodiment illustrated in FIGS. 1 and 2, fluid(s) "F" is provided to top portion 17*a* and is absorbed by the pores of top portion 17*a*. As the fluid "F" is absorbed by the pores of top portion 17*a*, the fluid "F" evaporates and cools bottom portion 17*b*.

Figure 3:
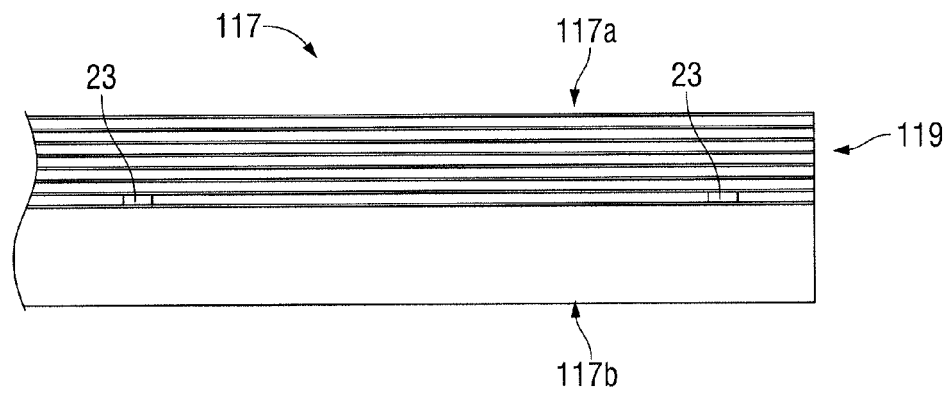
FIG. 3 is an enlarged, side, schematic view of a cutting blade configured for use with the ultrasonic instrument depicted in FIG. 1 according to another embodiment of the present disclosure.
Figure 4:
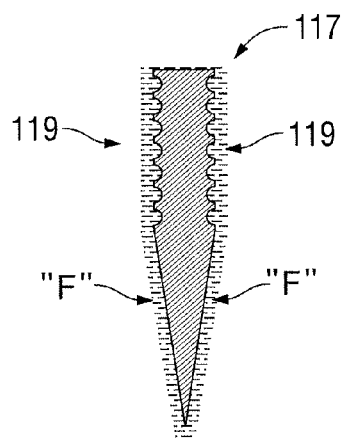
FIG. 4 is an enlarged, front view into the cutting blade depicted in FIG. 3.

In the embodiment illustrated in FIGS. 3 and 4, fluid(s) "F" is provided to top portion 117*a* and is configured to cool bottom portion 117*b*. In this instance, however, the fluid "F" is drawn into the longitudinal channels 119 via a capillary or wicking action and drips or trickles down the sides of top and bottom portions 117*a*, 117*b* to cool cutting blade 117, as best seen in FIG. 4.

Figure 5:
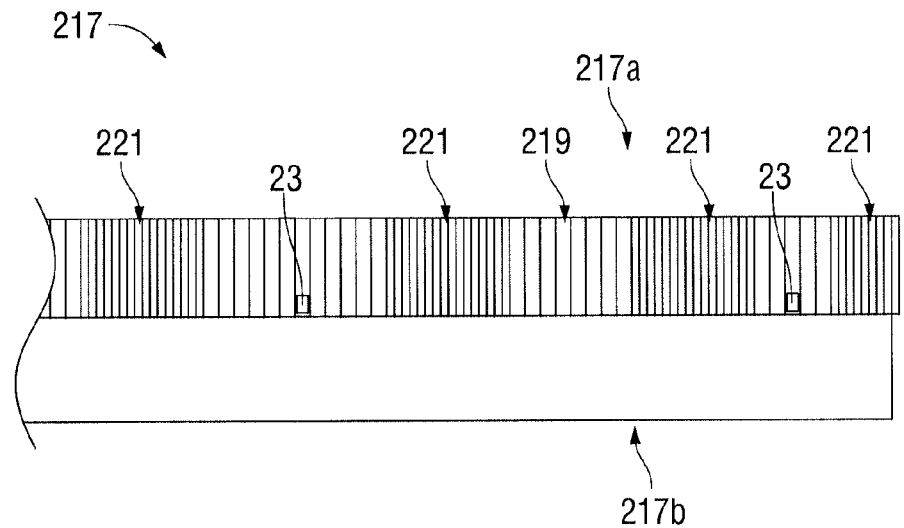
FIG. 5 is an enlarged, side, schematic view of a cutting blade configured for use with the ultrasonic instrument depicted in FIG. 1 according to another embodiment of the present disclosure.

In the embodiment illustrated in FIG. 5, the fluid(s) "F" is provided to top portion 217*a* and is configured to cool bottom portion 217*b*. In this instance, the fluid "F" is drawn into the plurality of grooves 219 via a capillary or wicking action and drips or trickles down the sides of top and bottom portions 217*a*, 217*b* to cool cutting blade 217. The plurality grooves 219 may be configured to include one or more nodes 221. Nodes 221 are segments along the top portion 217*a* that include more grooves 219 per a given area than other segments along top portion 217*a*, as best seen in FIG. 5. Providing nodes 221 along top portion 217*a* concentrates fluid(s) "F" to specific segments along bottom portion 217*b*, which facilitates cooling bottom portion 217*b*.

One or more temperature sensors 23 (FIGS. 2-3 and 5-6) may be positioned on cutting blades 17, 117, 217 and configured to detect a temperature of the cutting blades 17, 117, 217 during operation thereof. With this purpose in mind, temperature sensor(s) 23 may be any suitable type of temperature sensor including, but not limited to, thermocouples, thermistors and the like.

Temperature sensor(s) 23 may be configured to communicate with one or more modules of the generator 10 and/or the battery assembly 8. In one particular embodiment, for example, temperature sensor(s) 23 may be configured to provide data pertaining to a temperature of the cutting blades 17, 117, 217 to a temperature control module 11 (FIG. 1) of the generator 10 and/or battery assembly 8. In the illustrated embodiments, temperature control module 11 is provided with the generator 10 (FIG. 1). Temperature control module 11 may analyze the data pertaining to temperature of the cutting blades 17, 117, 217 and utilize one or more control algorithms to control an output of fluid to top portions 17*a*, 117*a*, 217*a* provided by fluid reservoir 29 such that a desired temperature may be maintained at the cutting blades 17, 117, 217. In one particular embodiment, temperature control module 11 may be configured to automatically control the output of fluid reservoir 29. Alternatively, fluid reservoir 29 may be controlled manually. For example, in embodiments, a switching mechanism 28 may be provided on housing 6 and in operative communication with reservoir 29 for control thereof. Switching mechanism 28 may be any suitable type of switching mechanism including but not limited to push-buttons, dials, slides, and the like. In accordance with the instant disclosure, switching mechanism 28 includes a dial 30 positioned at a distal end of the housing 6. Dial 30 is configured to communicate with reservoir 29 such that upon actuation of dial 30 fluid(s) "F" is provided from reservoir 29 to one of the aforementioned top portions 17*a*, 117*a*, 217*a*.

In one particular embodiment, instrument 2 and temperature control module 11 may be configured to provide one or more indications, e.g., an audio indication "A", a visual indication "V", and so forth, to a user indicating that the cutting blades 17, 117, 217 are heated beyond a predetermined safe temperature or sufficiently cooled to a predetermined safe temperature (FIG. 1). As defined herein, a safe temperature of the cutting blades 17, 117, 217 is a temperature incapable of damaging tissue.

During use of one particular embodiment of the instrument 2, tissue may be positioned between the jaw member 14 and one of the aforementioned cutting blades 17, 117, 217. Subsequently, trigger 7 may be depressed to activate the cutting blades 17, 117, 217 to treat tissue of interest.

The unique configuration of cutting blades 17, 117, 217 having a decreased thermal mass as a result of top portions 17*a*, 117*a*, 217*a* being configured differently than bottom portions 17*b*, 117*b*, 217*b* allows cutting blades 17, 117, 217 to dissipate heat faster, which, in turn, allows cutting blades 17, 117, 217 to operate at higher power levels, higher amplitudes, increased duty cycles, higher frequencies and/or for a longer period of time when compared to cutting blades associated with conventional ultrasonic instruments.

Moreover, as noted above, cutting blades 17, 117, 217 may become hot due to the vibratory motion thereof. In embodiments, reservoir 29 may be activated to provide fluid(s) "F" to top portions 17*a*, 117*a*, 217*a* to facilitate cooling cutting blades 17, 117, 217. In one particular embodiment, for example, sensor(s) 23 may send data pertaining to the temperature of bottom portions 17b, 117b, 217b to controller 11. In the instance where bottom portions 17b, 117b, 217b exceed a predetermined safe temperature, controller 11 may send a command signal to reservoir 29 calling for fluid(s) "F" to be sent to top portions 17a, 117a, 217a. Alternatively, controller 11 may provide an audio indication "A" or visual indication "V" to a user that bottom portions 17b, 117b, 217b have exceeded a predetermined safe temperature. In this particular embodiment, a user may actuate dial 30 to provide fluid(s) "F" to top portions 17a, 117a, 217a.

In either of the aforementioned embodiments, fluid(s) "F" may be provided to top portions 17a, 117a, 217a, which, in turn, provides fluid(s) to respective bottom portions, 17b, 117b, 217b to cool cutting blades 17, 117, 217.

Audio indication "A" or visual indication "V" may be provided to a user when cutting blade 17 is sufficiently cooled. As a result thereof, the likelihood of heat damage occurring to tissue adjacent tissue of interest that has been ultrasonically treated by the cutting blades 17, 117, 217 is reduced, if not eliminated.

From the foregoing and with reference to the various figure drawings, those skilled in the art will appreciate that certain modifications can also be made to the present disclosure without departing from the scope of the same. For example, in embodiments, top portion 17a, 117a, 217a may function as a heat sink and dissipate heat from respective bottom portions 17b, 117b, 217b into one or more suitable mediums, e.g., air, to facilitate cooling cutting blade 17, 117, 217. Thus, in embodiments, it may prove advantageous to form top portions 17a, 117a, 217a from material that includes a high thermal conductivity. In embodiments, it may prove advantageous to provide a portion of top portions 17a, 117a, 217a with diamond (or diamond dust), which has high thermal conductivity, to facilitate cooling bottom portions 17b, 117b, 217b of cutting blades 17, 117, 217.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
a housing having an elongated shaft extending therefrom, the shaft defining a longitudinal axis therethrough and having a jaw member disposed at a distal end thereof, the jaw member defining a first tissue-contacting surface; and
a cutting blade extending from the distal end of the shaft adjacent the jaw member and operably coupled to the housing, the cutting blade including a first portion formed of a porous ceramic material and a second portion formed of a non-porous material, the second portion defining a second tissue-contacting surface,
wherein the jaw member is movable relative to the cutting blade between an open configuration and a clamping configuration, and wherein, in the clamping configuration, the jaw member is configured to clamp tissue against the second portion of the cutting blade such that tissue contacts and is held between the first and second tissue-contacting surfaces, the first portion of the cutting blade configured to cool the second portion of the cutting blade while the second portion of the cutting blade treats tissue clamped between the first and second tissue-contacting surfaces.

2. The ultrasonic surgical instrument according to claim 1, wherein the material that forms the second portion is selected from the group consisting of stainless steel and titanium.

3. The ultrasonic surgical instrument according to claim 1, wherein a lever is operably coupled to the housing and is configured to move the jaw member between the open configuration and the clamping configuration.

4. The ultrasonic surgical instrument according to claim 1, wherein the first portion includes a side surface.

5. The ultrasonic surgical instrument according to claim 4, wherein the side surface defines at least one channel that extends along a length of the side surface.

6. The ultrasonic surgical instrument according to claim 4, wherein the side surface defines at least one groove that extends along a width of the side surface.

7. The ultrasonic surgical instrument according to claim 1, wherein the ultrasonic surgical instrument further includes a fluid reservoir disposed in the housing that is in fluid communication with at least one fluid conduit that extends through the shaft, wherein the at least one fluid conduit having a distal end disposed adjacent the first portion of the cutting blade.

8. The ultrasonic surgical instrument according to claim 1, wherein the jaw member includes at least one temperature sensor configured to detect a temperature of the second portion of the cutting blade.

9. The ultrasonic surgical instrument according to claim 8, wherein the at least one temperature sensor is selected from the group consisting of a thermocouple and a thermistor.

10. The ultrasonic surgical instrument according to claim 8, wherein the at least one temperature sensor is configured to communicate the detected temperature of the second portion to a controller operably associated with a generator of the ultrasonic surgical instrument.

11. The ultrasonic surgical instrument according to claim 10, wherein the controller is configured such that when the second portion of the cutting blade exceeds a predetermined temperature, the controller sends a command signal to the fluid reservoir calling for the at least one fluid to be delivered to the first portion of the cutting blade.

12. An ultrasonic surgical instrument, comprising:
a housing having a shaft extending therefrom, the shaft defining a longitudinal axis therethrough and having a jaw member disposed at a distal end thereof, the jaw member defining a first tissue-contacting surface; and
a cutting blade extending from a distal end of the shaft adjacent the jaw member and operably coupled to the housing, the cutting blade including a first portion formed of a porous material and a second portion formed of a non-porous material, the second portion defining a second tissue-contacting surface,
wherein the porous material is configured to permit penetration of fluid therethrough to enable cooling of the second portion of the cutting blade via evaporation of the fluid within the porous material while the second portion of the cutting blade treats tissue clamped between the first and second tissue-contacting surfaces.

13. The ultrasonic surgical instrument according to claim 12, wherein the ultrasonic surgical instrument further includes a fluid reservoir disposed in the housing that is in fluid communication with at least one fluid conduit that extends through the shaft, the at least one fluid conduit having a distal end disposed adjacent the first portion of the cutting blade for delivering fluid thereto for penetration through the porous material.

14. The ultrasonic surgical instrument according to claim 13, wherein the jaw member includes at least one temperature sensor configured to detect a temperature of the second portion of the cutting blade.

15. The ultrasonic surgical instrument according to claim 14, wherein the at least one temperature sensor is selected from the group consisting of a thermocouple and a thermistor.

16. The ultrasonic surgical instrument according to claim 14, wherein the at least one temperature sensor is configured to communicate the detected temperature of the second portion to a controller operably associated with a generator of the ultrasonic surgical instrument.

17. The ultrasonic surgical instrument according to claim 16, wherein the controller is configured such that when the second portion of the cutting blade exceeds a predetermined temperature, the controller sends a command signal to the fluid reservoir calling for the at least one fluid to be delivered to the first portion of the cutting blade.

18. The ultrasonic surgical instrument according to claim 12, wherein the porous material is a porous ceramic material.

\* \* \* \* \*